United States Patent [19]

Elliot

[11] Plant 4,747

[45] Jun. 30, 1981

[54] ROSE PLANT

[76] Inventor: Charles P. Elliot, 2208 Monterey Ave., Santa Clara, Calif. 95051

[21] Appl. No.: 145,330

[22] Filed: Apr. 30, 1980

[51] Int. Cl.[3] ..... A01H 5/00
[52] U.S. Cl. ..... Plt./18
[58] Field of Search ..... Plt./18–19

*Primary Examiner*—Robert E. Bagwill
*Attorney, Agent, or Firm*—Thomas E. Schatzel

[57] ABSTRACT

A new variety of rose plant originating as a cross between an unnamed seed parent and a pollen parent of the rose variety "Forever Yours" and characterized by its large regular pink blooms, vigorous growth, continuous blooming and persistence.

1 Drawing Figure

BACKGROUND OF THE NEW PLANT

The present invention comprises a new and distinct cultivar of rose plant which is a seedling cross-bred by the inventor in Santa Clara, Calif. The new seedling is a cross between an unnamed seed parent and a pollen parent of the rose variety known as "Forever Yours." The new seedling is a hybrid Tea Rose which has been named "Surain" by the inventor. The new seedling was selected from the offspring of the aforementioned cross in Santa Clara, Calif. and has been asexually reproduced by bud grafting at Santa Clara, Calif. and Newman, Calif. The new seedling has been found to retain its distinctive characteristics through successive propagations.

DESCRIPTION OF THE DRAWING

The accompanying drawing shows the unique characteristics of the new seedling, the color being as nearly true as possible with color illustrations of this type. The photograph shows the new seedling in full bloom.

DESCRIPTION OF THE NEW PLANT

The new seedling is a hybrid Tea Rose with a bright uniformly pink bloom. The seedling has been grown under greenhouse conditions in the vicinity of Watsonville, Calif. and has been found to have a continuously repeating year round blooming pattern under these conditions.

The new seedling is similar in some respects to the rose variety known as Carina, a well known commercial variety, and has generally the same characteristics as the Carina in so far as:

1. Height of plant.
2. Upright stature of plant.
3. Vigorous growth characteristics.
4. Large singly borne blooms.
5. Overall color of foliage.
6. Foliage shape.
7. Good persistence of petals.

The new seedling is distinguished from the Carina variety by the following characteristics:

1. Foliage is more abundant.
2. Foliage is firmer.
3. Foliage has notable ribs and veins on the underside.
4. Foliage has numerous serrations.
5. The stipules are reddish rather than green.
6. The arrangement of petals on the bloom is more regular.

7. Fragrance, although still slight, is more notable.
8. Bloom color is a different hue.
9. Bloom color is more uniform.
10. Stamens and anthers are shorter.
11. Styles are pink rather than white.
12. Ovaries are short rather than long.

In the description which follows, color references are made to the horticultural color chart, volumes I and II, issued by the British Colour Counsel in collaboration with the Royal Horticultural Society and copyrighted 1939 and 1941.

Botanical classification: Rosa Odorata.

Bud:
- *Size.*—Large.
- *Form.*—Long, urn-ovoid.
- *Sepals.*—Hooded above bud, curls back.
- *Calyx.*—Large, smooth, funnel shaped.
- *Peduncle.*—Long, heavy, smooth.

Color:
- *Initial sepal division.*—Tyrian Rose 24.
- *Initial unfurling.*—Phlox Pink 625.
- *Half blown; inside of petals.*—Spinel Pink o625/1.
- *Half blown; reverse of petals.*—Spinel Pink o625 to o625/3.

Bloom:
- *Size.*—4½".
- *Borne.*—Singly.
- *Stems.*—Long, strong.
- *Form.*—High center.
- *Permanence.*—Retains form.

Color:
- *Center of flower.*—Rose Opal o22/1.
- *Base of petals.*—Crimson 22/2.
- *Inside of petals.*—Rose Opal o22/1.
- *Reverse of petals.*—Rose Red 724/1.
- *Tonality from distance.*—Spinel Pink o625/1.

Petals:
- *Texture.*—Thick.
- *Appearance.*—Pointed.
- *Arrangement.*—Double, imbricated.
- *Persistence.*—Hang on and dry.
- *Fragrance.*—Slight, typical tea rose.

Reproductive organs:
- *Stamens, anthers.*—Medium, many, Yellow Ochre o7 with streaks of Spinel Pink o625, arranged regularly around styles.
- *Stamens, filaments.*—Medium threads, Spinel Pink o625.

*Pollen.*—Yellow Ochre o7/2–o7/3.
*Styles.*—Mixed size bunch, thin.
*Stigmas, tip.*—Yellow Ochre o7.
*Stigmas, base.*—Rose Opal o22/1.

Plant:

*Form.*—Bush.
*Growth.*—Vigorous, upright.
*Height.*—Greater than 1.6 meters (5 feet).
*Spread.*—Minimal, usually less than 1 meter (3 feet).

Foliage:

*Leaflets.*—Multiple, irregular, large, normal abundancy.
*Top side.*—Spinach Green o960.
*Under side.*—Sage Green ooo861.
*Shape.*—Pointed oval.
*Texture.*—Smooth.

*Ribs and veins.*—Ordinary.
*Edge.*—Serrated.
*Serrations.*—Single, small, sharp.
*Stipules.*—Medium.

Thorns:

*Quantity.*—Ordinary on main stalks, few on lateral stalks.
*Form.*—Narrow base, medium length, straight to slightly hooked downward.
*Color when young.*—Lettuce Green 861/3.
*Position.*—Irregular.

I claim:

1. A new and distinct cultivar of rose, substantially as described and pictured herein, characterized by its large regular pink blooms, vigorous growth, continuous blooming and persistence.

* * * * *

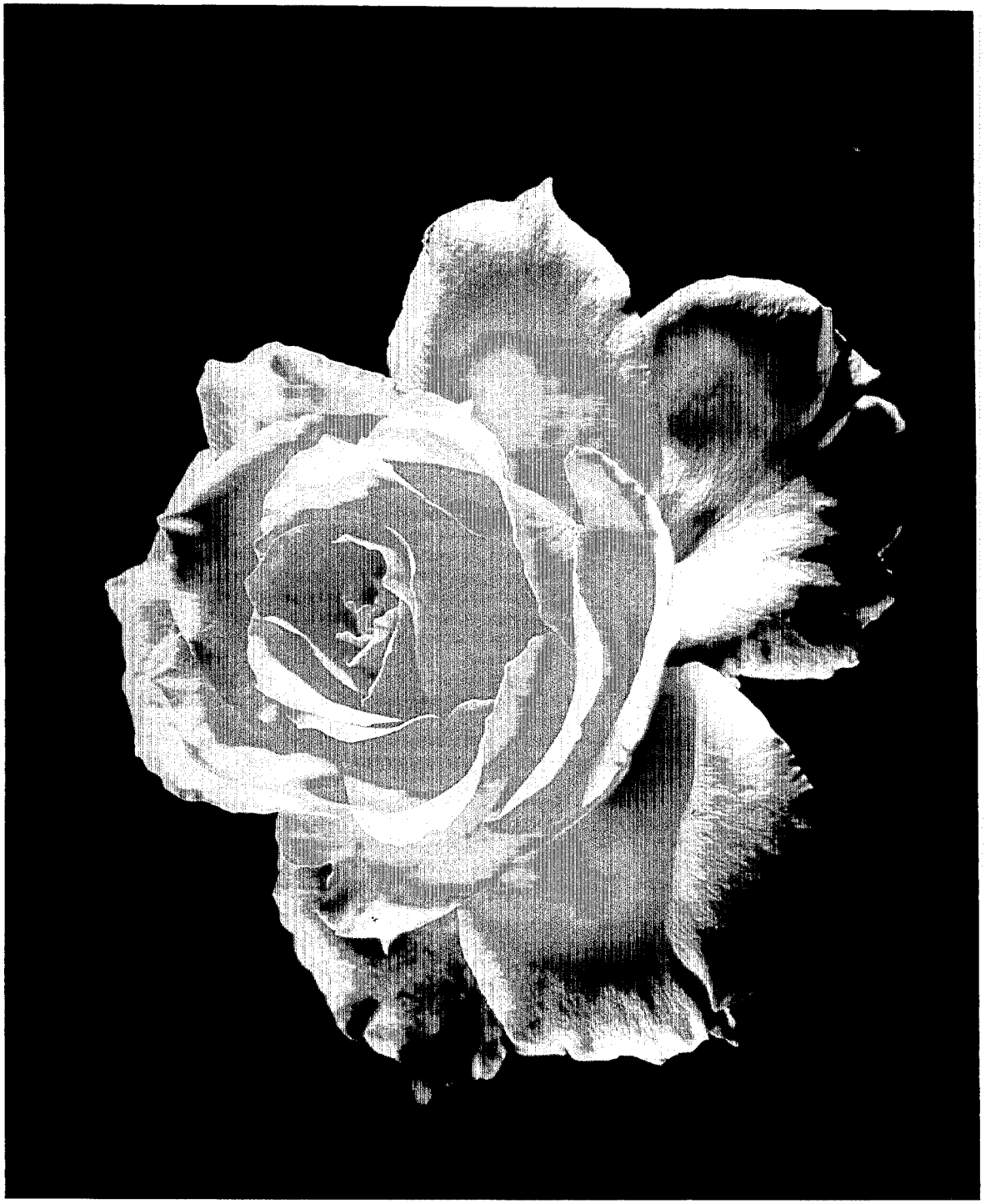

UNITED STATES PATENT OFFICE

CERTIFICATE OF CORRECTION

Patent No. Plant 4,747 Dated June 30, 1981

Inventor(s) Charles P. Elliott

It is certified that error appears in the above-identified patent and that said Letters Patent are hereby corrected as shown below:

On the Title page, the inventor's name should read --Charles P. Elliott--.
Column 2, line 5 "styles" should be --Filaments--.

Signed and Sealed this

Fifteenth Day of December 1981

[SEAL]

Attest:

GERALD J. MOSSINGHOFF

Attesting Officer

Commissioner of Patents and Trademarks

UNITED STATES PATENT OFFICE

CERTIFICATE OF CORRECTION

Patent No. PP 4,747 Dated June 30, 1981

Inventor(s) Charles P. Elliott

It is certified that error appears in the above-identified patent and that said Letters Patent are hereby corrected as shown below:

Column 2, line 13 "Odorata" should be --Hybrid Tea--.

Signed and Sealed this

*Twenty-ninth* Day of *May 1984*

[SEAL]

*Attest:*

GERALD J. MOSSINGHOFF

*Attesting Officer*

*Commissioner of Patents and Trademarks*